United States Patent
Batchelor et al.

(10) Patent No.: US 11,896,285 B2
(45) Date of Patent: Feb. 13, 2024

(54) DEVICE WITH MOVABLE BUTTONS OR SWITCHES AND VISUAL INDICATOR

(71) Applicant: GYRUS ACMI, INC., Southborough, MA (US)

(72) Inventors: Kester J. Batchelor, Mound, MN (US); Theodore C. Blus, Shoreview, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1622 days.

(21) Appl. No.: 15/921,351

(22) Filed: Mar. 14, 2018

(65) Prior Publication Data
US 2019/0282293 A1    Sep. 19, 2019

(51) Int. Cl.
*A61B 18/14*    (2006.01)
*A61N 7/00*    (2006.01)
(Continued)

(52) U.S. Cl.
CPC .......... *A61B 18/14* (2013.01); *A61B 18/1442* (2013.01); *A61N 7/00* (2013.01);
(Continued)

(58) Field of Classification Search
CPC ............... A61B 18/14; A61B 18/1442; A61B 2018/00958; A61B 2018/00946; A61B 2018/0922; A61B 2018/00309; A61B 2018/126; A61B 2018/1253; A61B 2018/00952; A61B 2018/00916;
(Continued)

(56) References Cited

U.S. PATENT DOCUMENTS 4,181,826 A    1/1980    Latasiewicz
4,256,931 A    3/1981    Palisek
(Continued)

FOREIGN PATENT DOCUMENTS

CN    110269673 A    9/2019
EP    1852078 A1    11/2007
(Continued)

OTHER PUBLICATIONS

English Translation of JP2008198501A (Year: 2008).*
(Continued)

*Primary Examiner* — Khadijeh A Vahdat
*Assistant Examiner* — Marina Delaney Templeton
(74) *Attorney, Agent, or Firm* — Schwegman Lundberg & Woessner, P.A.

(57) ABSTRACT

An electrosurgical device comprising: a) two or more functional states; b) a selector assembly that moves between at least a first position and a second position, the selector assembly including: i) one or more shuttles; ii) one or more buttons; iii) one or more circuit boards with one or more switches; and iv) one or more indicators; wherein the selector assembly in the first position is configured to provide a first one of the two or more functional states, and in the second position is configured to provide a second one of the two or more functional states; and wherein the one or more indicators communicates a first color, corresponding to the first functional state, and communicates a second color corresponding to the second functional state.

14 Claims, 8 Drawing Sheets

(51) Int. Cl.
  *A61B 90/00* (2016.01)
  *A61B 18/00* (2006.01)
  *A61B 17/00* (2006.01)

(52) U.S. Cl.
  CPC . *A61B 18/1402* (2013.01); *A61B 2017/00367* (2013.01); *A61B 2017/00429* (2013.01); *A61B 2018/00589* (2013.01); *A61B 2018/00595* (2013.01); *A61B 2018/00601* (2013.01); *A61B 2018/00607* (2013.01); *A61B 2018/00922* (2013.01); *A61B 2018/00946* (2013.01); *A61B 2018/00952* (2013.01); *A61B 2018/00958* (2013.01); *A61B 2018/1412* (2013.01); *A61B 2018/1455* (2013.01); *A61B 2018/1462* (2013.01); *A61B 2090/0807* (2016.02); *A61B 2090/0808* (2016.02); *A61B 2090/0811* (2016.02)

(58) Field of Classification Search
  CPC .. A61B 2018/00708; A61B 2018/0094; A61B 2017/00367; A61B 2017/00393; A61B 2017/00398; A61B 2017/00017; A61B 2017/00115; A61B 2017/2903; H01H 15/005; H01H 15/06; H01H 73/12; H01H 1/5805; H01H 11/04; H01H 13/023; H01H 13/12; H01H 13/52; H01H 71/04; H01H 71/58; H01H 2221/014
  USPC ... 606/41, 42, 43, 44, 45, 46, 47, 48, 49, 50
  See application file for complete search history.

(56) References Cited

U.S. PATENT DOCUMENTS

| | | |
|---|---|---|
| 4,319,099 A | 3/1982 | Asher |
| 4,504,707 A | 3/1985 | Ochiai |
| 4,688,569 A | 8/1987 | Rabinowitz |
| 4,703,139 A | 10/1987 | Dunlap |
| 4,800,878 A | 1/1989 | Cartmell |
| 4,802,476 A | 2/1989 | Noerenberg et al. |
| 4,846,516 A | 7/1989 | Yuh et al. |
| 5,035,695 A | 7/1991 | Weber, Jr. et al. |
| 5,071,426 A | 12/1991 | Dolgin et al. |
| 5,226,904 A | 7/1993 | Gentelia et al. |
| 5,282,799 A * | 2/1994 | Rydell ............... A61B 18/1402 604/35 |
| 5,376,765 A | 12/1994 | Holmes et al. |
| 5,399,823 A | 3/1995 | McCusker |
| 5,472,442 A | 12/1995 | Klicek |
| 5,663,532 A | 9/1997 | Dieken et al. |
| 5,743,384 A | 4/1998 | Clark |
| 5,762,613 A | 6/1998 | Sutton et al. |
| 6,110,171 A | 8/2000 | Rydell |
| 6,113,596 A | 9/2000 | Hooven et al. |
| 6,190,386 B1 | 2/2001 | Rydell |
| 6,193,714 B1 | 2/2001 | McGaffigan et al. |
| 6,310,308 B1 | 10/2001 | Watson et al. |
| 6,358,268 B1 | 3/2002 | Hunt et al. |
| 6,423,918 B1 | 7/2002 | King et al. |
| 6,551,313 B1 | 4/2003 | Levin |
| 6,590,508 B1 | 7/2003 | Howell et al. |
| 6,623,499 B1 | 9/2003 | Andreini et al. |
| 6,679,882 B1 | 1/2004 | Kornerup |
| 7,083,620 B2 | 8/2006 | Jahns et al. |
| 7,232,440 B2 | 6/2007 | Dumbauld et al. |
| 7,687,734 B2 | 3/2010 | Weber |
| 7,902,474 B2 | 3/2011 | Mittleman et al. |
| 8,089,017 B2 | 1/2012 | Chen et al. |
| 8,262,655 B2 | 9/2012 | Ghabrial et al. |
| 8,287,534 B2 | 10/2012 | Balog |
| 8,378,240 B2 | 2/2013 | Rajagopal et al. |
| 9,748,057 B2 | 8/2017 | Blus et al. |
| 9,959,996 B2 | 5/2018 | Casparian et al. |
| 2002/0038121 A1 | 3/2002 | Rozenberg et al. |
| 2005/0113827 A1 | 5/2005 | Dumbauld et al. |
| 2005/0130697 A1 | 6/2005 | Dyer |
| 2005/0187512 A1 | 8/2005 | Isola et al. |
| 2006/0084973 A1 | 4/2006 | Hushka |
| 2007/0049927 A1 | 3/2007 | Saltzman |
| 2008/0086117 A1 | 4/2008 | Cao |
| 2008/0312649 A1 * | 12/2008 | Guerra ............... A61B 18/1445 606/41 |
| 2010/0198200 A1 | 8/2010 | Horvath |
| 2011/0172659 A1 | 7/2011 | Brannan |
| 2011/0220479 A1 | 9/2011 | Zhou |
| 2012/0116267 A1 | 5/2012 | Kimball et al. |
| 2012/0123405 A1 | 5/2012 | Moua et al. |
| 2014/0048397 A1 | 2/2014 | Sykes et al. |
| 2014/0276795 A1 | 9/2014 | Batchelor et al. |
| 2014/0276797 A1 * | 9/2014 | Batchelor .......... A61B 18/1233 606/42 |
| 2014/0276799 A1 | 9/2014 | Batchelor et al. |
| 2014/0291380 A1 | 10/2014 | Weaner et al. |
| 2015/0076211 A1 | 3/2015 | Irka |
| 2016/0051314 A1 | 2/2016 | Batchelor |
| 2017/0194115 A1 | 7/2017 | Blus |
| 2017/0323744 A1 | 11/2017 | Blus et al. |
| 2017/0351341 A1 | 12/2017 | Norwalk et al. |
| 2020/0315685 A1 * | 10/2020 | Brady ............... A61B 18/1206 |

FOREIGN PATENT DOCUMENTS

| | | |
|---|---|---|
| EP | 1852078 A1 | 11/2007 |
| EP | 1897506 A1 | 3/2008 |
| EP | 1852078 B1 | 11/2010 |
| EP | 3539494 A1 | 9/2019 |
| JP | 2008198501 A * | 8/2008 |
| JP | 2019155077 A | 9/2019 |
| JP | 7217634 B2 | 1/2023 |
| JP | 2023038299 A | 3/2023 |

OTHER PUBLICATIONS

Extended European Search Report dated Aug. 12, 2019, Application No. 19151728.3.
Potentially Related U.S. Appl. No. 14/987,233, filed Jan. 4, 2016, published as US 2017/00194115 Sep. 6, 2017, and issued as Patent No. 9,748,057 Aug. 29, 2017.
Potentially Related U.S. Appl. No. 15/657,904, filed Jul. 24, 2017, published as US 2017/0323744 Nov. 9, 2017.
"Japanese Application Serial No. 2019-003219, Written Amendment filed Jan. 11, 2019", with English translation of claims, 4 pgs.

* cited by examiner

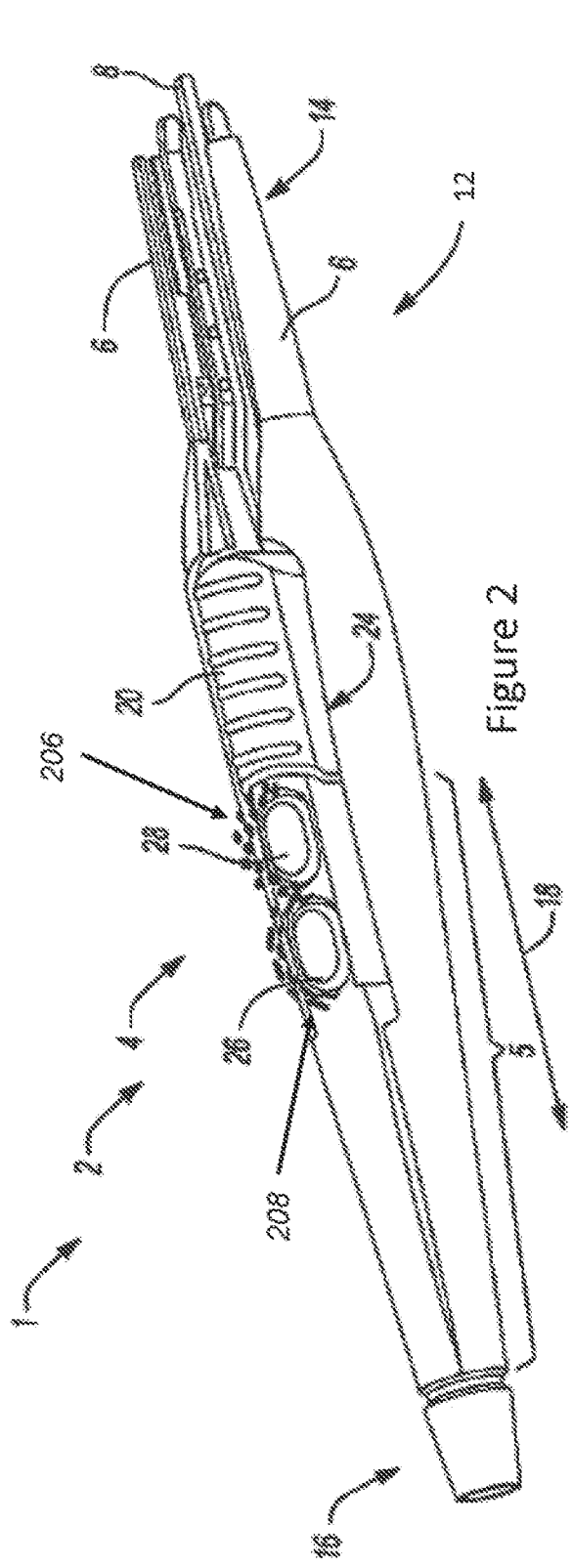
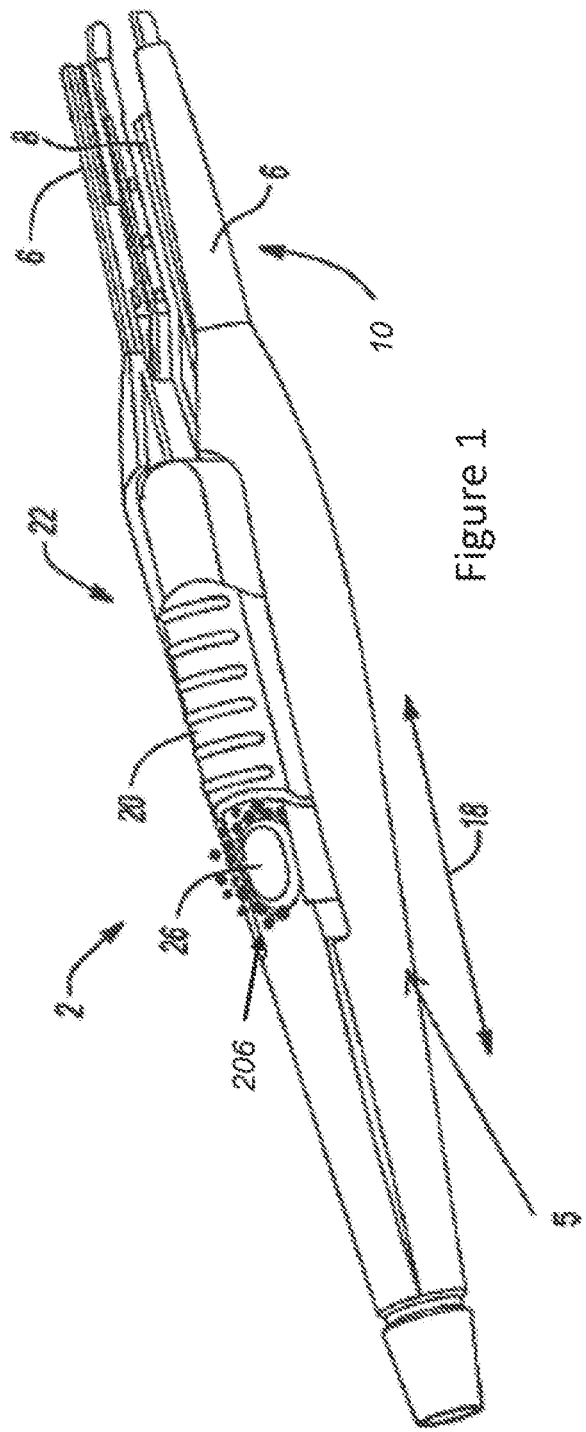

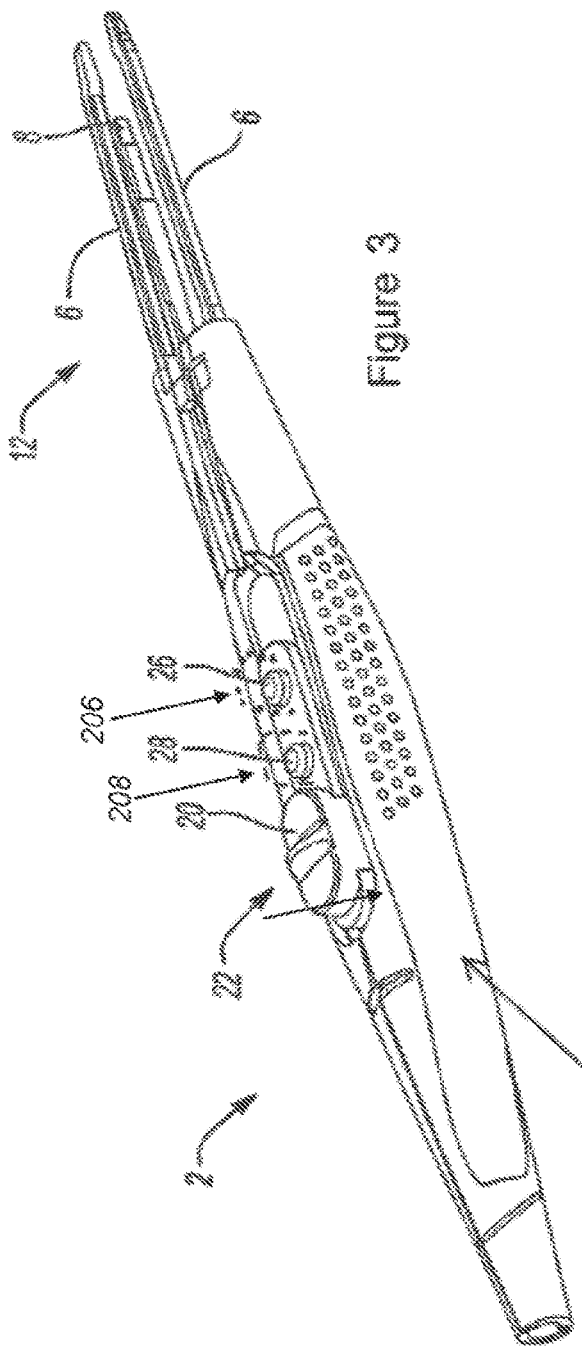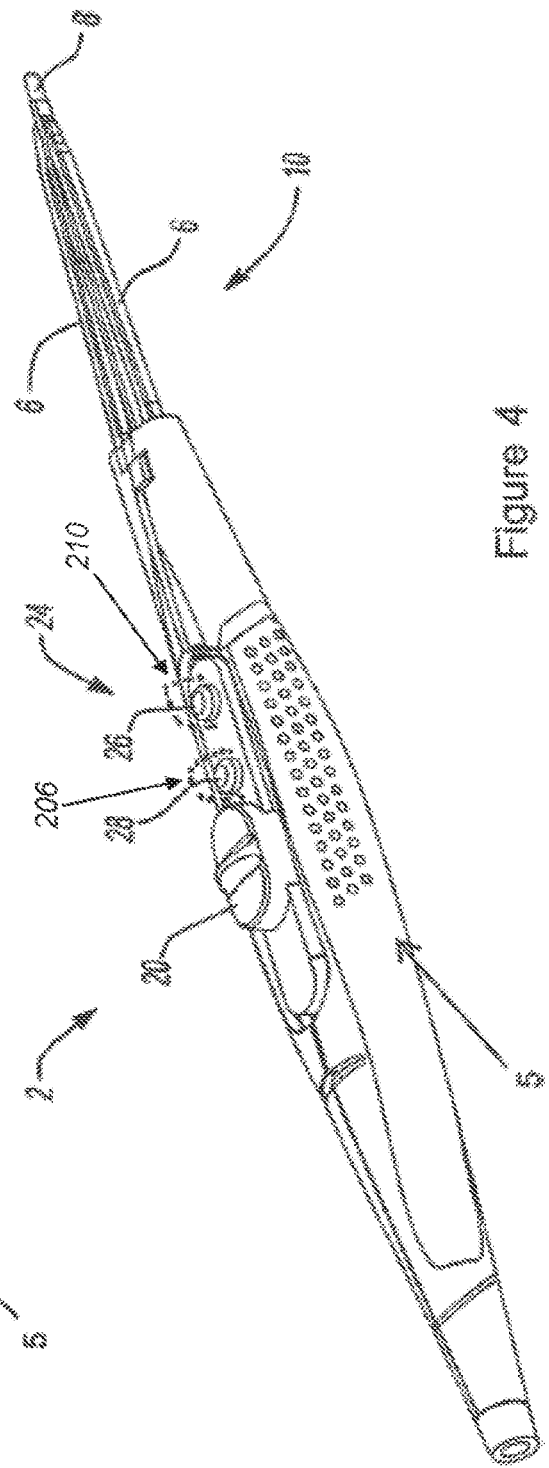

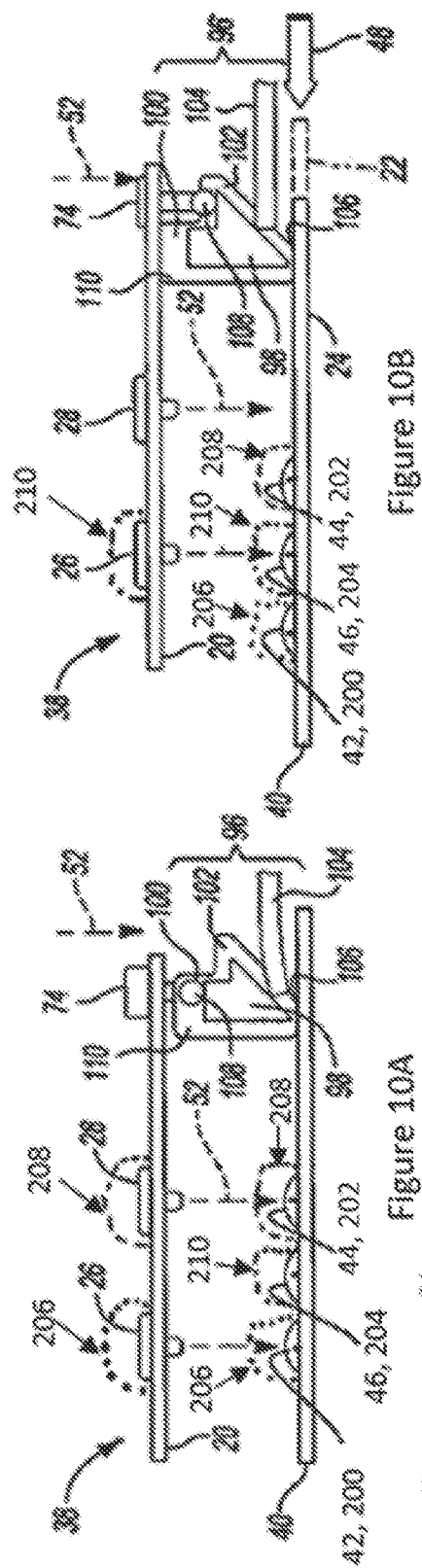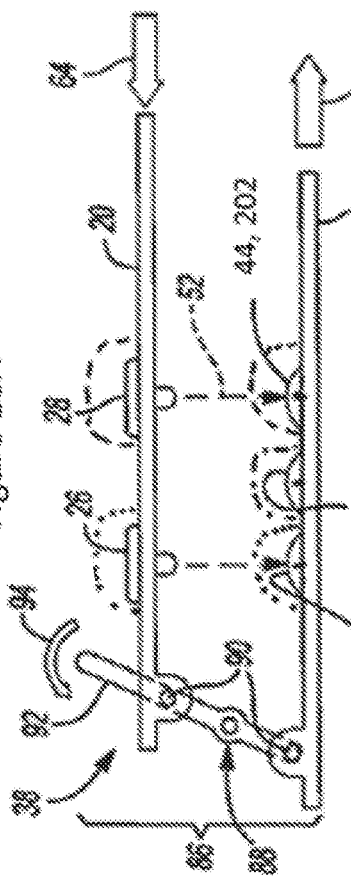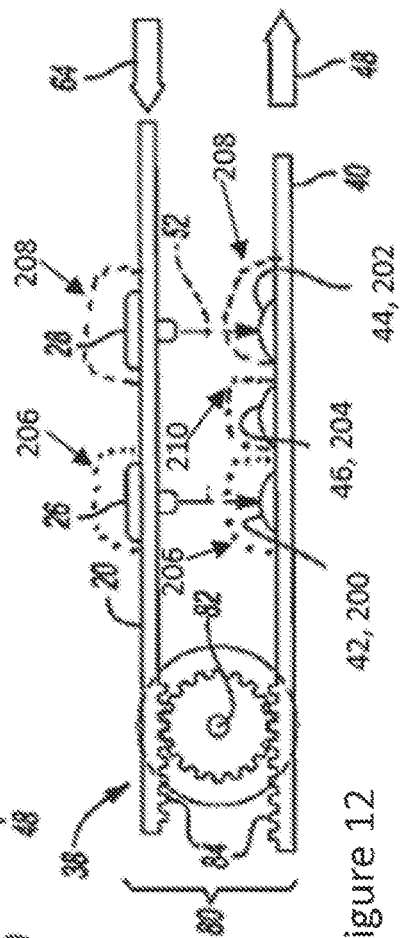

DEVICE WITH MOVABLE BUTTONS OR SWITCHES AND VISUAL INDICATOR

FIELD

The present teachings generally relate to devices, more specifically electrosurgical devices that include a circuit board switch and/or button that is repositionable between two or more positions so that two or more functional states are enabled and one or more indicators that identify each of the two or more functional states.

BACKGROUND

Typically, surgical devices have one functional element, thus if a different function is desired a surgeon will switch devices during a procedure to a device with a different function. However, some devices include a second functional element and each functional element is activated by actuating each individual button. For example, if the surgeon selects a device that has two buttons, one button activates monopolar cut and a second button activates bipolar coagulation. During surgery, the devices have different colored buttons that assist a user in identifying a function that the device is going to provide (e.g. a yellow button is cut; a blue button is coagulate). Thus, if a device provides multiple functions the device has a button for each function. When a device has one or more buttons with two or more functions, the surgeon may not be able to distinguish which therapy current (e.g. cut or coagulation) is provided upon actuation of the one or more buttons, which may lead to selecting the wrong function.

Examples of some electrosurgical instruments may be found in U.S. Pat. Nos. 6,110,171; 6,113,596; 6,190,386; 6,358,268; 7,232,440; and 9,748,057; and U.S. Patent Application Publication Nos. 2005/0113827; 2005/0187512; 2006/0084973; 2012/0123405; 2014/0276795; and 2014/0276799 all of which are incorporated by reference herein for all purposes. What is needed is a device that easily transforms between a plurality of different electrical states and functions while providing a visual indicator of which electrical state and function that is selected. It would be attractive to have a device that can switch between two or more states with a single button and the single button includes a visual indicator that indicates which of the two or more states have been selected. It would be attractive to have a device that mechanically reconfigures states so that the circuitry of the device physically changes position, electrically reconfiguring the device relative to the buttons while displaying a visual cue to the surgeon. What is needed is a device including a visual indicator that provides a signal through one or more buttons and the visual indicator identifies the electrical state that will be provided upon actuation of the one or more buttons.

SUMMARY

It would be attractive to have a device that provides one or more visual indicators, each visual indicator corresponding to a specific function so that a user is signaled to which function the device will perform before actuating one or more activation buttons.

The present teachings meet one or more of the present needs by providing: an electrosurgical device comprising: a) two or more functional states; b) a selector assembly that moves between at least a first position and a second position, the selector assembly including: i) one or more shuttles; ii) one or more buttons; iii) one or more circuit boards with one or more switches; and iv) one or more indicators; wherein the selector assembly in the first position is configured to provide a first one of the two or more functional states, and in the second position is configured to provide a second one of the two or more functional states; and wherein the one or more indicators communicates a first color, corresponding to the first functional state, and communicates a second color corresponding to the second functional state.

The present teachings comprise: an electrosurgical device comprising: a) two or more functional states; b) a shuttle that moves between at least a first position and a second position, the shuttle including one or more transparent buttons; and c) one or more indicators; wherein the shuttle moves the one or more transparent buttons into alignment with one of the one or more indicators so that a color from the one of the one or more indicators is visible through the one or more transparent buttons, signaling that the electrosurgical device is in one of the two or more functional states.

The teachings herein provide: an electrosurgical device comprising: a) two or more functional states; b) a shuttle that is movable between at least a first position and a second position, the shuttle including: i) one or more indicators; and ii) one or more circuit boards with one or more switches; c) one or more transparent buttons; wherein the shuttle in the first position aligns a first switch of the one or more switches with the one or more transparent buttons so that the electrosurgical device is configured in a first functional state of the two or more functional states and the one or more indicators transmit a first color through the one or more transparent buttons; wherein the shuttle in the second position aligns a second switch of the one or more switches with the one or more transparent buttons so that the electrosurgical device is configured in a second functional state of the two or more functional states and the one or more indicators transmit a second color through the one or more transparent buttons; wherein the one or more indicators aligns with the one or more transparent buttons in the first position and the second position, transmitting color through the one or more transparent buttons to a user; and wherein the first color indicates that the electrosurgical device is in the first functional state, and a second color indicates that the electrosurgical device is in the second functional state.

The teachings herein provide a surgical device that is reconfigurable between functional states to perform at least one function per functional state and a visual cue that is displayed from the device to a user, indicating which function is selected. The present teachings provide a device that can switch between two or more states with a single button and the single button includes a visual indicator that indicates which of the two or more states have been selected. The present teachings provide a device that mechanically reconfigures states so that the circuitry of the device physically changes position, electrically reconfiguring the device relative to the buttons while displaying a visual cue to the surgeon. The present teachings provide a device including a visual indicator that provides a signal through one or more buttons and the visual indicator identifies the electrical state that will be provided upon actuation of the one or more buttons.

BRIEF DESCRIPTION OF THE DRAWINGS

FIG. 1 is a perspective view of a surgical device in a first state;

FIG. 2 is a perspective view of a surgical device in a second state;

FIG. 3 is a perspective view of a surgical device in a first state;

FIG. 4 is a perspective view of a surgical device in a second state;

FIG. 10A is a perspective view of the selector assembly with a leaf spring mechanism in a first position;

FIG. 10B is a perspective view of the selector assembly with a leaf spring mechanism in a second position;

FIG. 11 is a perspective view of the selector assembly with a short throw lever assembly;

FIG. 12 is a perspective view of the selector assembly with a rack and pinion assembly.

DETAILED DESCRIPTION

Figure 5:
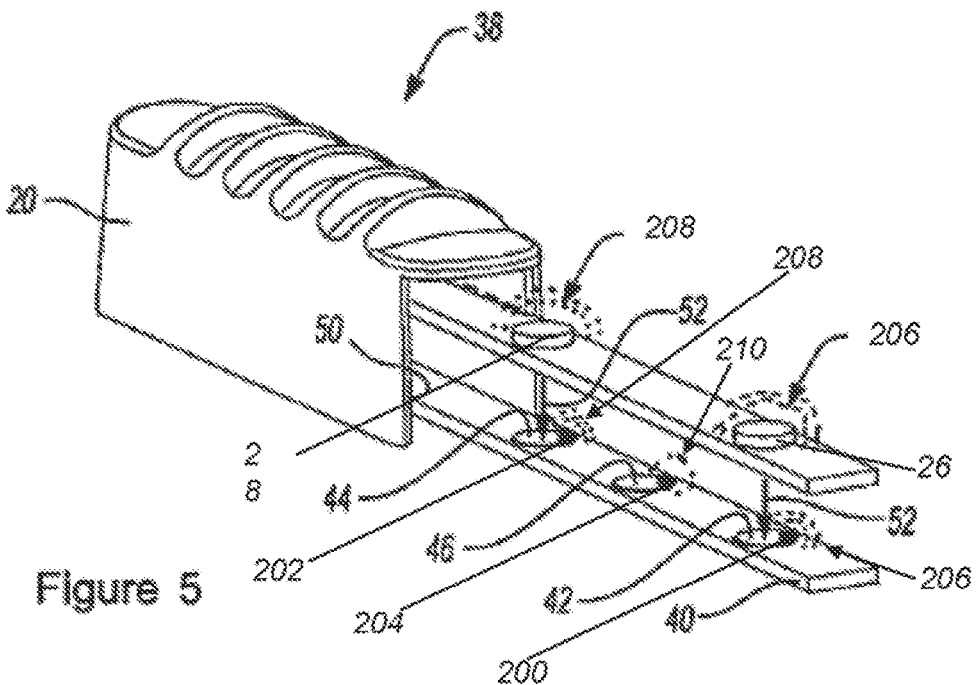
FIG. 5 is a perspective view of a selector assembly in a first position where the circuit board is moveable relative to the activation buttons.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a device that may be changeable between two or more states. The surgical device may be a mechanical device, an electromechanical device (e.g., a device with a mechanically moving element and an electrical element), an electrosurgical device, or a combination thereof. The device may be any device that functions to generate a signal, provide power, or both. The device may transmit a first set of signals in a first state and a second set of signals in a second state. The device may include one or more buttons or one or more keys. The one or more buttons or one or more keys may provide two or more signals depending on the position or state of the keys or buttons (buttons and keys as discussed herein are used interchangeably). The keys, buttons, or both and a circuit board may be movable relative to each other to create different signals so that the device provides different functions. The circuit board, keys, buttons, or a combination thereof may include one or more indicators. The one or more indicators may function to provide a user a visual cue to indicate which state the device is in. The one or more buttons, one or more keys, or both may be present on a keyboard, a phone, computer, surgical device, or a combination thereof. The present teachings may relate to buttons on a surgical device. The present teachings may relate to a surgical device and associated componentry that form an electronic, ultrasonic, or motorized surgical system or a combination thereof. The present teaching may relate to a convertible surgical device with one or more visual indicators.

The surgical device may be a part of a surgical system. The surgical system may be any system that includes one or more of the devices taught herein. The surgical system may include at least a surgical device with at least one functional state (e.g., configuration). The functional state may be a relative disposition or arrangement of any part of the device that moves relative to another part. For example, the selector assembly may move the buttons relative to the circuit board or vice versa so that the device changes between a first functional state (or first configuration) and a second functional state (or second configuration). The surgical system may include one or more bodies as taught herein, one or more ground pads, one or more generators, one or more electrosurgical devices, one or more ultrasonic devices, one or more motorized devices, one or more adjacent body components, or a combination thereof and the teachings herein of each device, which are incorporated into the surgical system. The surgical device may be any device that may be used by a surgeon to perform a surgical procedure. The surgical device may function to be switched between two or more configurations, two or more states, or both. For example, the surgical device may be switched between an electrical state, an ultrasonic state, a motorized state, a non-powered state, or a combination thereof. The surgical device may be any device that may be switched between two or more states with one hand so that a user may switch between the states without the need for a second hand, without disrupting the procedure, or both. The surgical device may be any device and/or state that may be used ambidextrously, ambidextrously switched between states, or both. The surgical device may be used to cut, perform hemostasis, coagulate, desiccate, fulgrate, electrocautery, or a combination thereof. The surgical device may perform one or more functions. Preferably, the surgical device performs a plurality of functions. For example, the surgical device may perform a first function, second function, third function, fourth function, or more functions. The surgical device may be any device that includes bipolar capabilities, monopolar capabilities, non-electrosurgical capabilities, ultrasonic capabilities, motorized capabilities (e.g. powered movement to cut, grind, saw, drill or a combination thereof), or a combination thereof. The surgical device may display a signal corresponding to each function through the one or more indicators. For example, the one or more indicators may display a first cue to signal a monopolar therapy current and display a second cue to signal a bipolar therapy current. The surgical device may be used in open surgery. The surgical device may be used for non-powered surgical purposes. For example, the surgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The surgical device may include a handpiece and a generator. The surgical device may have one or more therapy signals that extend between the handpiece and the generator. The hand piece may be a body.

The surgical device may have a body. The body may function to connect a functional element to a user interface. The body may provide power, signals, or both to the function element. The body and one or more functional elements may be one integral piece or the functional element may be removable from the body. The body may include a power source or be connected to a power source. The body of the device may house the components that are used to make the device functional. The body of the device may be a hand piece. The body of the device may be forceps. The body of the device may be a frame. The body of the device may connect working arms, one or more functional elements, or both. The body of the device may include or be connected to one or more activation buttons, one or more circuit boards, a shuttle, one or more functional elements, a selector assembly, one or more indicators, or a combination thereof.

The surgical device may include a selector assembly. The selector assembly may function to change the device between multiple functional states. The selector assembly may change the functional state of the one or more activation buttons by moving the one or more activation buttons, the one or more circuit boards, or both. The selector assembly may be changeable between two or more positions so that each of the one or more activation buttons provide two or more functions. For example, the surgical device may perform or provide more functions than activation buttons that are present on the device (e.g., one button may activate 2 or more, 3 or more, 4 or more, or even 5 or more functions). The selector assembly may longitudinally move along the surgical device (e.g., may move along in the direction of the longitudinal axis of the device); rotationally move around a component of the surgical device (e.g., the selector assembly may follow the contour of the surgical device in a direction substantially perpendicular to the longitudinal axis); the selector assembly may laterally move (e.g., from side to side without following the contour of the device); or a combination thereof. The longitudinal axis as discussed herein is the dimension with the longest length. The selector assembly may include one or more position transmitters. The selector assembly may communicate which position the surgical device is in to a generator, one or more circuit boards, one or more indicators, or a combination thereof. The selector assembly may activate and deactivate one or more indicators depending on the position of the selector assembly. For example, the selector assembly may actuate one or more position transmitters to send a position signal to a generator connected to one or more circuit boards of the surgical device, the generator then sends the position signal to the one or more indicators, turning the indicators on or off. In another example, the selector assembly may send a position signal from the one or more position transmitters to the generator, the generator then transmits the position information to the one or more indicators so that the visual output of the one or more indicators changes from a first visual cue in a first position to a second visual cue in a second position. The selector assembly may move along or within one or more channels. The selector assembly may be moveable by a sliding action, a leaf spring mechanism, a short throw lever assembly, a rack and pinion assembly, or a combination thereof. The selector assembly may include a portion that is located on a surface of the surgical device and a portion that extends into the surgical device. The selector assembly may change position through the use of a position change button. The position change button may be in communication with a mechanism or assembly that may allow for the selector assembly to move between positions when depressed. The selector assembly may be on the body, removably attached to a body, movable along the body, or a combination thereof. The selector assembly may include one or more shuttles, one or more activation buttons, one or more circuit boards, a position change button, a leaf spring mechanism, a short throw lever assembly, a rack and pinion assembly, or a combination thereof.

The selector assembly may include one or more position transmitters. The one or more position transmitters may function to communicate the position of the surgical device to a generator, one or more circuit boards, one or more indicators, or a combination thereof. The one or more position transmitters may be one or more discrete switches. The one or more position transmitters may be one or more encoders. The one or more position transmitters may be a combination of discrete switches and encoders. The one or more transmitters may be mechanical, optical, magnetic, capacitive, or a combination thereof. The one or more position transmitters may be located on the selector assembly, a body, one or more circuit boards, one or more indicators, or a combination thereof. For example, the one or more position transmitters are located on a stationary circuit board so that when the selector assembly is moved from a first position to a second position, the one or more position transmitters are actuated, relaying the position information to a generator, a circuit, one or more indicators, or a combination thereof. In another example, the one or more position transmitters may be located on a moveable circuit board, so that when the selector assembly is moved from a first position to a second position, the movable circuit board is also moved from the first position to the second position, actuating the one or more position transmitters associated with the second position, relaying the position information to a generator, a circuit, one or more indicators, or a combination thereof. In a further example, the one or more position transmitters are a first position transmitter and a second position transmitter located on a circuit board, so that in the first position a shuttle actuates the first position transmitter while the second position transmitter is free from actuation, and actuates the second position transmitter in the second position, while the first position transmitter is free from actuation. The one or more position transmitters upon actuation by the shuttle relay the position information to a generator, a circuit, one or more indicators, or a combination thereof.

The selector assembly may include one or more moveable shuttles. The one or more shuttles may function to carry the one or more activation buttons, the one or more circuit boards, one or more encoders, one or more discrete switches, or a combination thereof. The one or more shuttles may function to assist in converting the surgical device between functional states. The shuttle may be moveable relative to the body of the surgical device. The shuttle may move the device between a plurality of functional states (e.g., electrical states). For example, the device may be moved from a first state to a second state. The device may be moved between a first state, second state, third state, fourth state, or more states. The shuttle may move along a line or axis of the device; along a surface of the device; pivot as a lever on the device; rotate as a knob on the device; or a combination thereof. The shuttle may move between positions (e.g., first, second, third, or fourth positions) as the shuttle moves along the device. The shuttle may longitudinally move along the surgical device (e.g., may move in the direction of the longitudinal axis of the device); rotationally move around a component of the surgical device (e.g., may follow the contour of the surgical device in a direction substantially perpendicular to the longitudinal axis); the shuttle may laterally move (e.g., from side to side without following the contour of the device); or a combination thereof. The shuttle may move along the longitudinal axis of the surgical device. The shuttle may move in a direction substantially perpendicular to the longitudinal axis (i.e., laterally). The shuttle may move around a rotational axis that is substantially parallel to the longitudinal axis (i.e., rotationally). The shuttle may carry one or more position transmitters, which determine the position of the surgical device and relay the information to the generator, the one or more circuit boards, the one or more indicators, or a combination thereof. The shuttle may actuate one or more position transmitters, communicating the position of the surgical device to the generator, the one or more circuit boards, the one or more indicators, or a combination thereof. The shuttle may include one or more of a leaf spring mechanism, a short throw lever assembly, or a rack and pinion assembly that assist in moving the shuttle. The shuttle may be in communication with the one or more activation buttons, the one or more circuit boards, the one or more indicators or a combination thereof. For example, the shuttle may be in communication with and move the one or more activation buttons relative to the one or more circuit boards and the body of the surgical device. In another example, the shuttle may be in communication with and move the one or more circuit boards relative to the one or more activation buttons and the body of the surgical device. In a further example, the shuttle may be in communication with both the one or more circuit boards and the one or more activation buttons, such that the one or more activation buttons and the one or more circuit boards move relative to each other. The shuttle may have two or more positions (e.g., at least a first position and a second position). The shuttle may have a plurality of positions. The shuttle may have a first position, second position, third position, fourth position, or more. The shuttle may disable one or more of the functional states in one or more of the positions discussed herein. The shuttle may disable a second electrical state in a first position and disable a first electrical state and/or a third electrical state in a second position. For example, the shuttle may be positioned so that the first electrical state is disabled in the second position. The shuttle may help to convert the surgical device between functional states based on the shuttle's position. For example, the shuttle may place the surgical device in the first state in the first position and places the surgical device in the second state when the shuttle is moved into the second position. The shuttle may align one or more activation buttons with one or more circuit board switches, one or more circuit board switches on a second circuit board, or both in a first position. The shuttle may misalign the one or more activation buttons with a first circuit board switch and align the activation buttons with the second circuit board switches, or vice versa in a first position. Alignment may be when the button can move into contact with a switch. More particularly, alignment may be when the button can move linearly and substantially perpendicularly to the switch so that the switch is activated upon movement of the button. Misalignment may be where the button, when acted upon, does not contact a switch and does not activate a switch. The shuttle may align one or more of the activation buttons with one or more of the circuit board switches, one or more second circuit board switches, or both in the second position. The shuttle may be placed in two or more positions so that the one or more activation buttons align with or misalign with the one or more circuit board switches on the one or more circuit boards.

The selector assembly may include a position change button. The position change button may function to convert the device between two or more positions. The position change button may be in communication with a mechanism or assembly to convert the device between positions (e.g., from a first position to a second position). The position change button may engage a mechanism or assembly when actuated to move the selector assembly from one position to another position by moving the shuttle, the circuit board, the activation buttons, or a combination thereof by converting mechanical potential energy into directional movement. The position change button may be located on the exterior of the device. The position change button may include an actuator. The position change button may act upon a leaf spring mechanism, a short throw lever assembly, a rack and pinion assembly, or a combination thereof.

The selector assembly may include a leaf spring mechanism. The leaf spring mechanism may convert the device between functional states (e.g., a first state and a second state). The leaf spring mechanism may include a position change button, an actuator block with a track, a plunger, a leaf spring, or a combination thereof. The actuator block may attach to a circuit board, a shuttle, one or more activation buttons, or a combination thereof. The actuator block may have a track. The actuator block track may be on the interior, exterior, or both of the handpiece. The actuator block track may have at least one position. The position change button may be used to convert the leaf spring mechanism between positions. The position change button may include a plunger. The plunger may fit into the track of the actuator block. For example, when the position change button is acted upon, the position change button plunger may move between two or more positions of the actuator block. When the position change button plunger moves, the actuator block may change position so that the leaf spring can push the actuator block, which is connected to the shuttle, the activation buttons, the circuit board, or a combination thereof. The force of the leaf spring expanding may be converted into directional movement, moving the device into another position. When the actuator block is moved from one position to another position, the circuit board, the shuttle, the one or more activation buttons, or combination thereof may be moved relative to each other through the transformation of the potential energy stored in the leaf spring into directional movement.

The selector assembly may include a short throw lever assembly. The short throw lever assembly may be used to convert the device between a plurality of states (e.g., a first state and a second state). The short throw lever assembly may change the position of the selector assembly from one position to another when actuated. The short throw lever assembly may include a lever, a fixed pivot point, one or more moving pivot points, or a combination thereof. The lever may attach to the shuttle, the circuit board, the activation buttons, or a combination thereof at one of the one or more moving pivot points. The lever may pivot about a fixed point. The lever may pivot around the fixed point pushing or pulling the circuit board, the shuttle, the activation buttons, or a combination thereof when a force is put onto the lever. The short throw lever assembly may move the activation buttons and circuit board into alignment or misalignment. The short throw lever assembly may move the selector assembly by moving the circuit board, the shuttle, the one or more activation buttons, or a combination thereof relative to each other, converting the device from one state to another state.

The selector assembly may include a rack and pinion assembly. The rack and pinion assembly may be used to convert the device between a first state and a second state. The rack and pinion assembly may assist in changing the position of the selector assembly from one position to another position. The rack and pinion assembly may include a pinion gear, and one or more rack gears. The rack and pinion assembly may move the selector assembly through rotating a pinion gear in communication with one or more of the rack gears connected with the activation buttons, the shuttle, the circuit board, or a combination thereof. The teeth of the pinion gear may intertwine with the teeth of the rack, which may be connected to the circuit board, the activation buttons, the shuttle, or a combination thereof, moving the circuit board and the activation buttons into alignment or misalignment with one another when the assembly is rotated.

The surgical device may include one or more activation buttons. The one or more activation buttons may function to active or deactivate the functional elements. The one or more activation buttons may function to convey a visual cue from one or more indicators to a user. The one or more activation buttons may actuate one or more circuit board switches, align with one or more circuit board switches, align with one or more indicators or a combination thereof. The one or more activation buttons may be a plurality of activation buttons. The one or more activation buttons may be a first activation button, a second activation button, a third activation button, a fourth activation button, or even a plurality of activation buttons. For example, each actuation button may actuate one or more circuit board switches so that a plurality of functions may be provided by the surgical device. The one or more activation buttons may contact (e.g., through direct contact or indirect contact) a circuit board switch (e.g., a dome or membrane) to initiate one or more of the functional elements. The one or more activation buttons may move substantially linearly (e.g., perpendicularly to the switches). Each of the one or more activation buttons may provide a different function, control a different functional element, provide multiple functions through the same functional element, or a combination thereof. The one or more activation buttons may provide a different function in each position and/or functional state. For example, one activation button may align with a first circuit board switch to enable a first function upon actuation in a first position, and align with a second circuit board switch to enable a second function upon actuation in a second position. The one or more activation buttons may be located on the body of the surgical device, on the shuttle, or both. The activation button when depressed actuates a circuit board switch so that one or more of the functional elements of the surgical device are activated. The circuit board switch may be actuated when the activation button is depressed, which completes a circuit and powers one or more of the functional elements. There may be more than one activation button present on the surgical device. For example, there are a plurality of activation buttons. The one or more of the activation buttons may have a plurality of positions. For example, each of the one or more activation buttons may be moved between a first position and a second position. The one or more activation buttons may carry one or more indicators. The one or more activation buttons may be transparent, translucent, opaque, opaque with a transparent window, opaque with a translucent window, or a combination thereof. The one or more buttons may be opaque and located proximate to a transparent or translucent window and a visual signal indicating the functionality of each of the one or more activation buttons may be indicated through the window. The one or more activation buttons may align with one or more indicators. The one or more activation buttons may align with one or more, two or more, three or more, four or more, or a plurality of indicators. The one or more activation buttons may allow the one or more indicators to be seen by a user. For example, the one or more activation buttons may be transparent and align with one or more indicators, the one or more indicators transmitting a visual cue through the one or more transparent activation buttons to be seen by a user. The one or more activation buttons when aligned with an indicator may activate the indicator so that a visual cue is transmitted. The one or more activation buttons may be longitudinally moveable along the longitudinal axis of the device, laterally moveable along a secondary dimension of the device (e.g., a direction substantially perpendicular to the longitudinal axis), rotatably moveable about the rotational axis, or a combination thereof. Preferably, the one or more activation buttons will move about the longitudinal axis. The one or more activation buttons may be static. The one or more activation buttons may be static relative to the body, to the shuttle, circuit board, or a combination thereof. The one or more activation buttons may be a rigid element, non-conductive element, or both. The one or more activation buttons may be constrained from motion by guides in the body. The one or more activation buttons when aligned with the circuit board or circuit board switches (i.e., electrosurgical switches) may contact the circuit board or circuit board switches when depressed, activating one or more functional elements.

The surgical device may include a circuit board. The circuit board functions to activate or deactivate one or more of the functional elements. The circuit board may function to receive one or more user inputs, receive one or more position signals, control one or more functional elements of the surgical device, or a combination thereof. The circuit board may function to convey position information from the one or more position transmitters to the generator, the one or more indicators, or both. The surgical device may include more than one circuit board. The surgical device may have one or more, two or more, three or more, four or more, or a plurality of circuit boards. The circuit board may have surface mounted circuitry, through-hole circuitry, or both. For example, the circuit board may have surface mounted circuitry. The circuit board may have components mounted or placed onto the surface. For example, all of the circuit componentry, including the circuit board switch, are mounted on the top surface of the circuit board to allow the circuit board to be mounted flat onto the mounting surface of the device. The circuit board may be in communication with one or more position transmitters. The one or more position transmitters may be located on the circuit board. The circuit board may be immediately adjacent to the one or more position transmitters. The circuit board may carry the one or more indicators. The one or more circuit boards may control the visual output of the one or more indicators based on the actuation of the one or more position transmitters. The one or more circuit boards may turn the one or more indicators on and/or off based on the actuation of the one or more position transmitters. The circuit board may be of a through-hole construction. Through-hole construction fits the components with wire leads into holes in the circuit board. When more than one circuit board is present, the circuit boards may be movable relative to each other. For example, one circuit board may be moved over or under another circuit board so that a different function may be activated. One circuit board may be movable and one circuit board may be static. Both circuit boards may be movable. The one or more circuit boards may be located on or within the body of the surgical device, on or within the shuttle, or both. The one or more circuit boards may activate a functional element of the surgical device. The one or more circuit boards may have at least one switch per circuit board that interact with the one or more activation buttons. The circuit board switches may be surface mounted switches. When the circuit board switch is actuated by the depressed activation button, the circuit board switch closes a circuit of the circuit board and enables the functional element of the surgical device. The one or more circuit boards may have one or more indicators per switch located on the one or more circuit boards. The one or more circuit boards may have one position transmitter per position of the surgical device. The one or more circuit boards may actuate one or more position transmitters, communicating the position of the surgical device to one or more indicators, changing the visual cue of the one or more transmitters depending on the position of the surgical device. There may be more than one circuit board present on the surgical device. The surgical device may include a plurality of circuit boards. For example, the surgical device may have a first circuit board and a second circuit board. The first circuit board may enable a first functional element when actuated and the second circuit board enables a second functional element when actuated. The surgical device may have one activation button that moves between two circuit boards and aligns with the first circuit board when in the first position and the second circuit board in the second position. In the first position, the second circuit board may be misaligned with the activation button and may be misaligned with activation button in the second position. Preferably the one or more of the circuit boards may have a plurality of positions. For example, each of the one or more circuit boards may be moved between a first position and a second position. The one or more circuit boards may be longitudinally moveable along the longitudinal axis of the device, laterally moveable along a secondary dimension of the device (e.g., substantially perpendicular to the longitudinal axis), rotatably moveable about the rotational axis (e.g., an axis that is parallel to the longitudinal axis), or a combination thereof. Preferably, the one or more circuit boards will move about the longitudinal axis. The one or more circuit boards may be static. The one or more circuit boards may be static relative to the body, to the shuttle, the activation buttons, or a combination thereof. There may be more than one circuit board switches on a circuit board. For example, there may be two circuit board switches located on the same circuit board (e.g., a first circuit board switch and a second circuit board switch). There may be more than one indicator on a circuit board. For example, there may be two indicators located on the same circuit board (e.g. a first indicator and a second indicator). For example, both a first circuit board and a second circuit board may include a first circuit board switch with a first indicator and a second circuit board switch with a second indicator. In the example, when the first circuit board switch is depressed, a first function is performed and when the second circuit board switch is depressed, a second function is performed.

The one or more circuit boards include one or more circuit board switches. The circuit board switches may function to enable the surgical device to activate functional elements through interacting with the circuit board and the one or more activation buttons. Each of the circuit boards may include one or more switches and preferably a plurality of switches. The one or more switches may be a first switch, a second switch, a third switch, a fourth switch, a fifth switch, or more switches. The surgical device may include the same number of switches as buttons. For example, the surgical device may include two buttons and two switches. The surgical device may include the same number of indicators as switches. For example, the surgical device may include two switches and two indicators. The surgical device may include a different number of buttons and switches. For example, the device may include three switches and one button. In another example, the surgical device may include two buttons and three switches. The surgical device may include a different number of switches and indicators. For example, the surgical device may include one indicator and two switches. The one or more circuit board switches may be flat, convex, concave, a dome switch, a membrane switch, an electrical switch, a capacitive sensor, a pressure sensor, or a combination thereof. Preferably, the one or more circuit board switches may be a dome switch. The one or more circuit board switches interact with the one or more activation buttons when the one or more activation buttons are aligned with the circuit board switches such that when the one or more activation buttons are depressed, the buttons make contact with and engage the one or more circuit board switches to complete the circuit, enabling a functional element of the surgical device. The circuit board switches may be activated without being contacted. For example, depression of an activation button may create a field that triggers the circuit board switch so that a function is activated. The one or more circuit board switches may be the one or more indicators. The one or more circuit board switches may be connected to the one or more indicators.

The surgical device may include one or more indicators. The one or more indicators may function to visually notify a user of which position and/or function the surgical device provides. The one or more indicators may be one or more, two or more, three or more, four or more, or even five or more indicators. The one or more indicators may be a colored device. The one or more indicators may be a colored portion of the circuit board, the one or more circuit board switches, or both. The one or more indicators may be a light emitting device (e.g. light emitting diode). The one or more indicators may always produce a visual cue (e.g., the indicators may always produce a light and the light is only visible when the indicator and a button are aligned). The one or more indicators may be turned on and off by the circuit board when a position signal is sent from the one or more position transmitters. For example, a first indicator may be illuminated in a first position when a first position transmitter is actuated, sending a signal to the circuit board to power the first indicator, and a second indicator is not illuminated. A second indicator may be illuminated in a second position when a second position transmitter is actuated and the first indicator is not illuminated. The one or more indicators may be color changing. The one or more indicators may have one or more, two or more, three or more, four or more, or even a plurality of colors. The one or more indicators may change from one visual cue to another visual cue by the circuit board when a position signal is sent from the one or more position transmitters. For example, an indicator may have a first visual output when the surgical device is in the first position because the one or more position transmitters signal to the circuit board that the surgical device is in the first position, and the indicator may have a second visual out (e.g. a second color) when the surgical device is in the second position because the one or more position transmitters signal to the circuit board that the device is in the second position. The one or more indicators may be located on the one or more circuit boards, the one or more circuit board switches, the selector assembly, the shuttle, the body, the one or more activation buttons, or a combination thereof. The one or more indicators may align and misalign with the one or more activation buttons, the one or more circuit boards, the one or more circuit board switches, one or more indicator windows, or a combination thereof. For example, the one or more indicators may be a first indicator with a first color and a second indicator with a second color and may be located on a circuit board with a first switch and a second switch, and the first indicator and the first switch may align with a transparent activation button in the first position, and the second indicator and the second switch may align with the transparent activation button in a second position. A first color may be visible through the transparent activation button in the first position and the second color may be visible through the transparent activation button in the second position. In another example, a first indicator may align with one or more translucent or transparent indicator windows located adjacent to one or more activation buttons so that the indicator transmits a visual cue through the one or more indicator windows to a user. Each color may indicate a particular function so that a user can ascertain which function will be applied when the one or more activation buttons are actuated. In another example, the one or more indicators may be a color-changing LED located on a circuit board so that a first color is visible through a transparent activation button in a first position and a second color is visible through the same transparent activation button in a second position. In this example, the LED may change color when the surgical device changes from the first position to the second position to indicate that the activation button may signal a different function between in the first position than in the second position. The one or more circuit board switches, the one or more activation buttons, and the one or more indicators may be brought into or out of alignment by changing the position of the selector assembly, which may change the functional state of the surgical device.

The functional state of the surgical device may be changeable so that a functional element may be activated. The surgical device may have one or more, two or more, three or more, four or more, five or more, or even a plurality of functional states. Each of the functional states may provide one or more different functions. For example, the first functional state may be a forceps that provides a bipolar therapy current and a second functional state may be a probe that provides a monopolar therapy current. The surgical device may create a first functional state when the selector assembly is in the first position. The selector assembly in the first position may position one or more circuit board switches and one or more indicators in alignment with at least one of the activation buttons, so that a first color is visible through the activation button. The activation button may be positioned to contact a circuit board switch, completing a circuit and enabling a first function when the activation button is engaged.

The functional second state may change the surgical device into a secondary form to allow a second functional element to be used. The second functional state may be enabled when the selector assembly is in the second position. The selector assembly may be advanced into the second position which may move either the one or more circuit boards or the one or more activation buttons, forming the second functional state. Upon moving the one or more circuit boards or one or more activation buttons, the previously enabled function may no longer be accessible due to the misalignment and/or realignment of the activation buttons relative to the circuit board switches. The surgical device in the second functional state may misalign one or more of the activation buttons with one or more of the circuit board switches so that the misaligned activation button is effectively disabled. The selector assembly may be moved into the second position to form the second functional state, so that the one or more activation buttons and the one or more circuit board switches may be misaligned, so when the activation button is depressed, the button does not contact the circuit board switch, disabling the functional element. The second functional state of the surgical device may realign one of the activation buttons with one of the circuit board switches and one or more indicators so that a second functional element may be activated, wherein the second functional element is different than the functional element activated in the first state. For example, a first activation button aligns with a first circuit board switch and a first indicator to provide a first visual cue corresponding to a first function that is enabled upon actuation in the first position, and the first activation button misaligns with the first circuit board switch and the first indicator, aligning with a second circuit board switch and a second indicator to provide a second visual cue corresponding to a second function that is enabled upon actuation in the second position. The shuttle in the second functional state may be in the second position so that at least one of the activation buttons may be aligned with another circuit board switch to enable a second functional element that is different than the first functional element. The one or more indicators may have a second color associated with the second functional element to visually indicate to a user that the second functional element is selected. For example, the first functional element may produce a first therapy current with a first color displayed by the one or more indicators, and the second functional element may be a second therapy current with a second color displayed by the one or more indicators. For example, the surgical device may have a first and a second activation button that align with a first and a second circuit board switch and corresponding first and second indicators, so that two different visual cues are displayed from each of the activation buttons in the first position, notifying a user of the two different functions (e.g. a first electrical element and a second electrical element) enabled in the first position upon actuation. The surgical device may change from the first position to the second position, aligning the first button with the second circuit board switch and the second indicator, and the second button with a third circuit board switch with a third function (e.g. third electrical element) and a third indicator, so that the second visual cue is displayed through the first button and the third visual cue is displayed through the second button, notifying a user that the first button now enables the second functional element and the second button now enables the third functional element upon actuation of each of the activation buttons.

The one or more functional elements may be electrical elements. The one or more functional elements may use electricity to perform one or more portions of a surgical procedure. One or more electrical elements may be functional elements that use electricity to operate. The one or more electrical elements may be an electrode, an electrical motor, an ultrasonic transducer, or a combination thereof. The one or more electrical elements may be an electrode, a first therapy current, a second therapy current, a third therapy current, a motor, an ultrasonic transducer, or a combination thereof. The first electrical element may be operated in a first position and the second electrical element may be operated in a second position. The surgical device may have one or more, two or more, three or more, four or more, or even a plurality of electrical elements. Each of the electrical elements may have a corresponding color so that the one or more indicators can indicate to a user which electrical element is selected.

The one or more electrical elements may include one or more electrodes. The electrodes may conduct electricity through the surgical device upon activation. The electrodes may conduct therapy currents. A therapy current may be a monopolar current, bipolar current, or a combination thereof. The therapy current may be used to cut, cauterize, coagulate, or a combination thereof during a surgery. The electrodes may conduct a therapy current that is used to actuate a motor. Each therapy current may have a particularly color associated to it. For example, a first therapy current is may be a monopolar current and the associated color is blue, and a second therapy current may be a bipolar current and the associated color is yellow, so that the one or more indicators display a blue color when the monopolar current is enabled, and display yellow when the bipolar current is enabled.

The functional element of the surgical device may be an ultrasonic component. The ultrasonic functional element may be used to identify a targeted area, cut, coagulate, or a combination thereof. For Example, the ultrasonic element may cut and coagulate by converting the electrical energy to mechanical vibration that is applied to tissue. Ultrasonic capabilities may be combined with a monopolar function, a bipolar function, or both. For example, the device in a first state may be actuated to produce ultrasonic energy to cut a targeted area, and the device in a second state may actuate a bipolar therapy current to coagulate a targeted area. In a further example, the device in the first state sends ultrasonic energy to a targeted area, and in the second state sends both ultrasonic and bipolar energy to a targeted area to simultaneously cut and coagulate. The ultrasonic element may have its own designated color displayed by the one or more indicators.

The surgical device may be a combination device. A combination device incorporates two or more structural elements into a single device to make a tool that is capable of performing multiple functions without switching handsets.

FIG. 1 illustrates a perspective view of the electrosurgical device 2 with the shuttle 20 (along the longitudinal axis 18) in the first position 22 and the blade electrode 8 in the first functional state 10 so that the blade electrode 8 is retracted between the pair of working arms 6. When the shuttle 20 is in the first position 22 the first activation button 26 is exposed. The first activation button 26 is transparent or translucent and communicates a first color 206.

FIG. 2 illustrates a perspective view of one example of a surgical device 1 that is shown as an electrosurgical device 2. The electrosurgical device 2 is shown as forceps 4 having a body 5 with a distal end 14 and a proximal end 16. The distal end 14 includes a pair of working arms 6 with a blade electrode 8 there between. The blade electrode 8 is advanced forward into a second functional state 12 when the shuttle 20 is moved forward into a second position 24 (i.e. along the longitudinal axis 18). In the second position 24, both the first activation button 26 and the second activation button 28 are shown. The first activation button 26 displays a second color 208 produced by a second indicator (not shown). The second activation button 28 displays a first color 206 produced by a first indicator (not shown). The first indicator and the second indicator are located on the circuit board, so that when the shuttle 20 is moved from the first position 22 to the second position 24, the circuit board also moves the first indicator and the second indicator, reconfiguring the device to provide both a first function and a second function. Moving between the first position 22 and the second position 24, the first indicator is aligned with the second activation button 28, displaying the first color 206 and the second indicator is aligned with the first activation button 26, displaying the second color 208. Each functional element has a corresponding color.

FIG. 3 illustrates a perspective view of an electrosurgical device 2 with a shuttle 20 in the first position 22. In the first position 22, the first activation button 26 and second activation button 28 are exposed and the blade electrode 8 is retracted between the working arms 6 so that a first functional state 10 is created. The first activation button 26 transmits a first color 206 from a first indicator (not shown). The second activation button 28 transmits a second color 208 from a second indicator (not shown).

FIG. 4 illustrates a perspective view of an electrosurgical device 2 with the shuttle 20 in the second position 24. As shown, both a first activation button 26 and a second activation button 28 are exposed for providing power to the blade electrode 8. The first activation button and the second activation button are moved from the first position 22 (FIG. 3) to the second position 24. The circuit board (not shown) is stationary. The circuit board holds a first indicator, a second indicator, and a third indicator, so that when the surgical device is moved from position to position, the activation buttons 26, 28 align with the corresponding indicators to visually notify a user which function will be enabled upon actuation of a particular activation button 26, 28. The first activation button 26 displays the third color 210, and the second activation button 28 displays the first color 206. The blade electrode 8 is advanced forward into the second functional state 12 so that the blade electrode 8 extends beyond the pair of opposing working arms 6.

FIG. 5 illustrates a selector assembly 38 including a shuttle 20 connected to a circuit board 40 at a connection region 50. The printed circuit board 40 includes a plurality of switches (e.g., a first circuit board switch 42 and a second circuit board switch 44). A first indicator 200 is located on the first circuit board switch 42 and a second indicator 202 is located on the second circuit board switch 44. A third indicator 204 is located on the third circuit board switch 46. As illustrated, a first activation button 26 is aligned with the first circuit board switch 42 and the first indicator 200, and a second activation button 28 is aligned with a second circuit board switch 44 and the second indicator 202. The first indicator 200 displays a first color 206 and the second indicator displays a second color 208, corresponding to the function that will be perform upon actuation of the activation buttons 26, 28. When the first activation button 26 and/or second activation button 28 are actuated in the direction 52, contact is created with the first circuit board switch 42 and the second circuit board switch 44, respectively. The third circuit board switch 46 and third indicator are misaligned with the activation buttons so that a third color 210 is not displayed through the activation buttons 26, 28.

Figure 6:
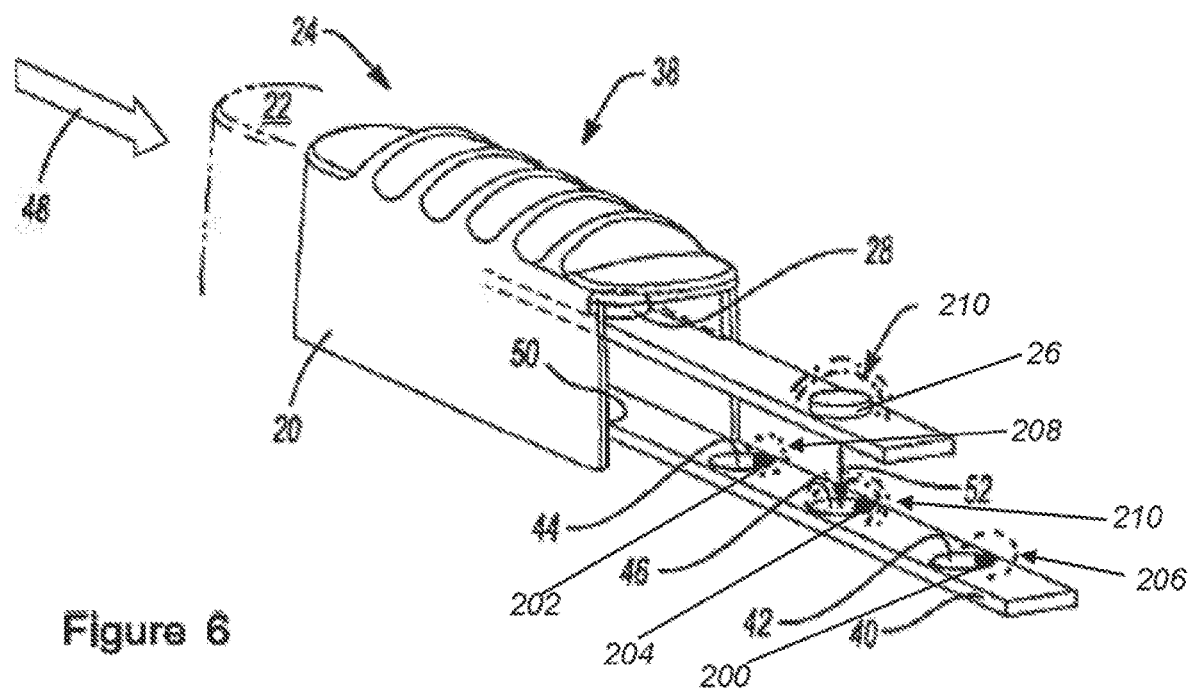
FIG. 6 is a perspective view of a selector assembly in a second position where the circuit board is moveable relative to the activation buttons.

FIG. 6 illustrates the selector assembly 38 including shuttle 20 and circuit board 40 that are moved in the direction 48 so that the third circuit board switch 46 and third indicator 204 are aligned with the first activation button 26. The third indicator 204 displays the third color 210 through the first activation button 26. The shuttle 20 and the circuit board 40 are connected together at a connection region 50 and move in unison. When the shuttle 20 is moved from the first position 22 into the second position 24, the second activation button 28 is covered and misaligned so the activation button 28 does not contact any circuit board switch when actuated. The first circuit board switch 42 with the first indicator 200 and the second circuit board switch 44 with the second indicator 202 are misaligned with the activation buttons 26, 28 so that the first color 206 and the second color 208 are not visible through the activation buttons. The blade electrode (not shown) is retracted.

Figure 7:
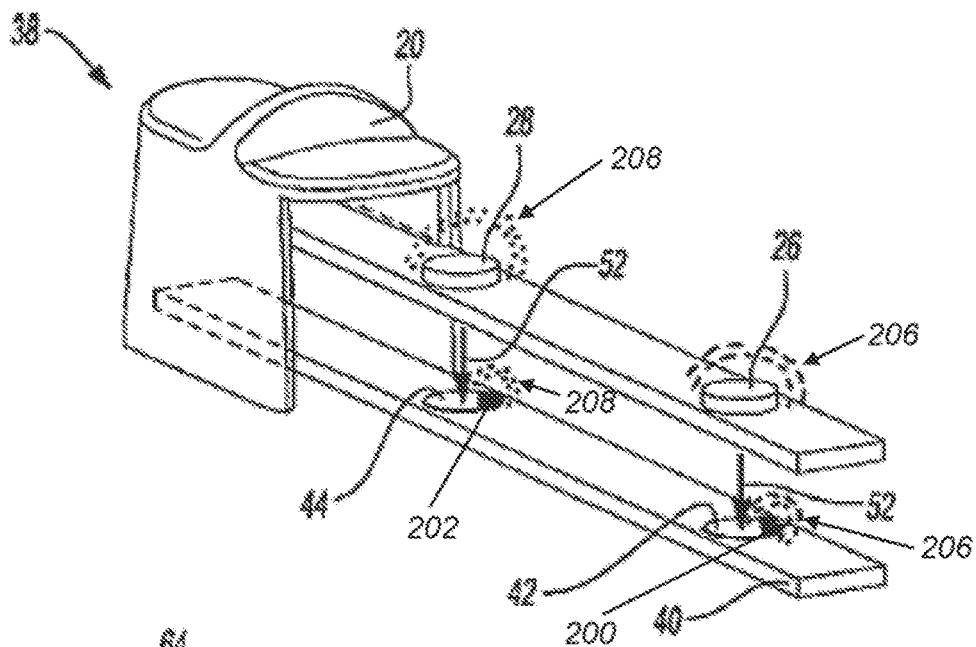
FIG. 7 is a perspective view of a selector assembly in a first position where the activation buttons are moveable relative to the circuit board.

FIG. 7 illustrates a selector assembly 38 including shuttle 20, and activation buttons 26, 28. The circuit board 40 includes a first circuit board switch 42 and a second electrosurgical switch 44. The first circuit board switch 42 includes a first indicator 200 which displays a first color 206. The second circuit board switch 44 includes a second indicator 202 which displays a second color 208. As illustrated, a first activation button 26 is aligned with the first circuit board switch 42 and a second activation button 28 is aligned with the second circuit board switch 44 so that when the first activation button 26 or second activation button 28 are actuated in the direction 52 contact is created with the first circuit board switch 42 and the second circuit board switch 44, respectively. The first indicator 200 transmits the first color 206 through the first activation button 26 to a user. The second indicator 202 transmits the second color 208 through the second activation button 28 to a user.

Figure 8:
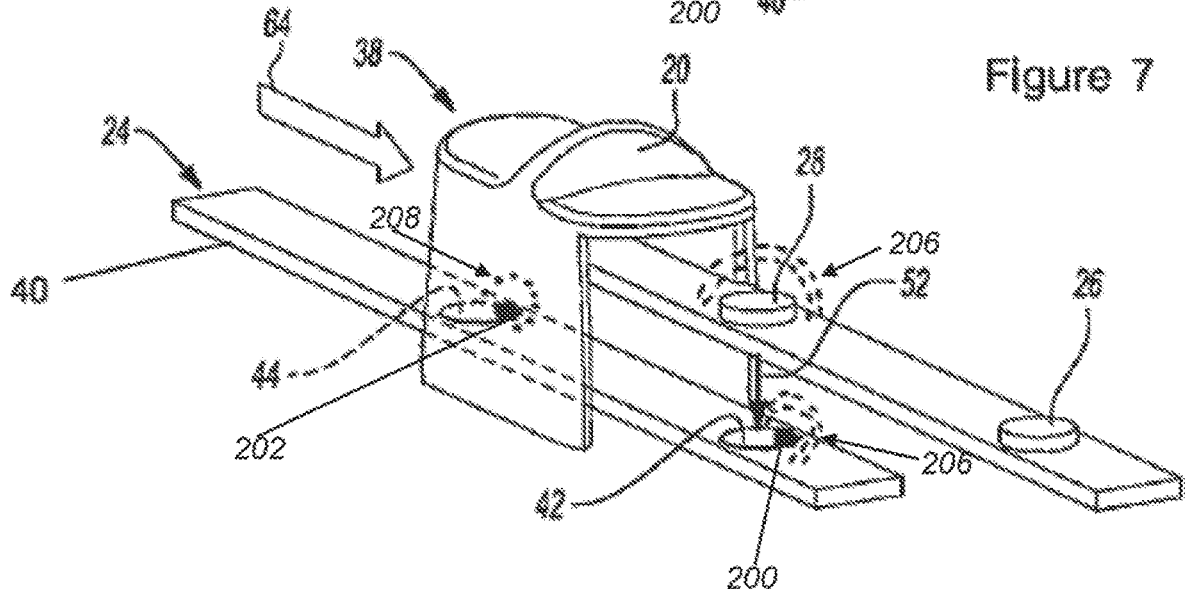
FIG. 8 is a perspective view of a selector assembly in a second position where the activation buttons are moveable relative to the circuit board.

FIG. 8 illustrates the selector assembly 38 including shuttle 20 and activation buttons 26, 28 moved in the direction 64 so that the second activation button 28 is aligned with the first circuit board switch 42 and the first indicator 200 so that when the second activation button 28 is moved in the direction 52, the second activation button contacts the first circuit board switch 42 and the first color 206 is displayed through the second activation button 28. The first activation button 26 is positioned so that it does not interact with the circuit board switches 42, 44. The second circuit 44 board switch is positioned so it cannot be actuated by either activation button 26 and 28. The shuttle 20 includes the activation buttons 26, 28 and move in unison in direction 64 to place the device in position two 24.

Figure 9A:
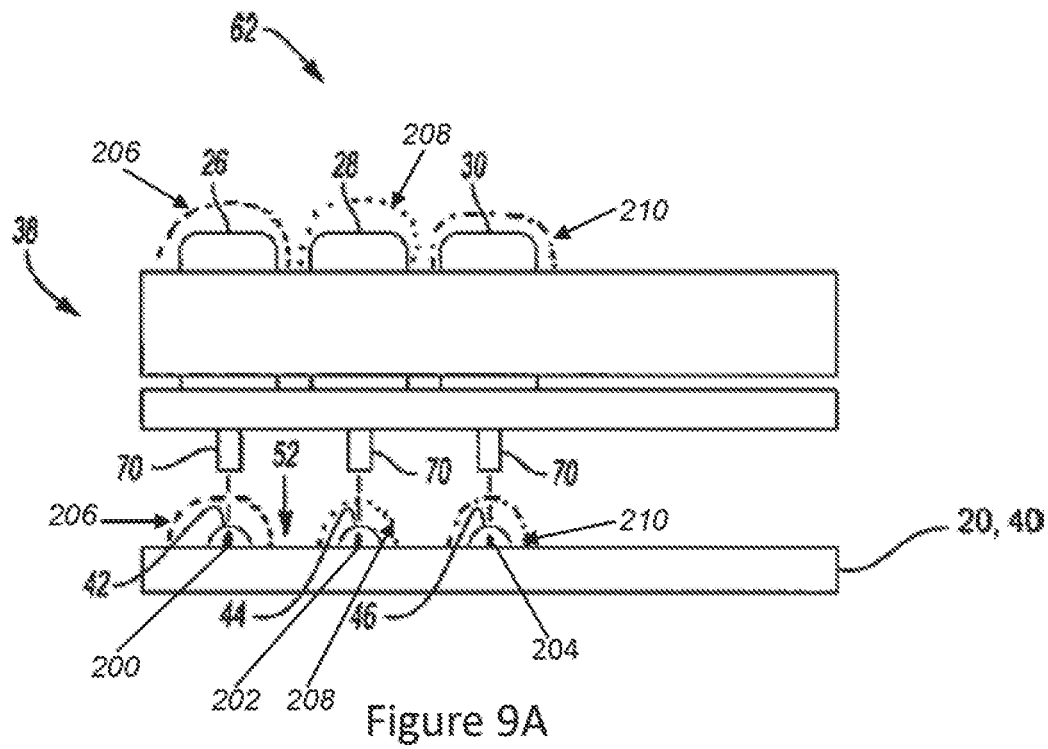
FIG. 9A is a perspective view of the device as a keyboard in a first position.

FIG. 9A illustrates the selector assembly 38 as a keyboard 62 with multiple activation buttons 26, 28, 30 aligned with multiple circuit board switches 42, 44, 46 located on the circuit board 40. When one or more of the activation buttons 26, 28, 30 are depressed in direction 52, one or more of the circuit board switches 42, 44, 46 are actuated, respectively. Each circuit board 42, 44, 46 has a corresponding indicator 200, 202, 206. Each indicator displays a particular visual cue 206, 208, 210 that is transmitted to a user when aligned with one of the buttons 26, 28, 30. As shown, indicator 200 is aligned with button 26 which displays the first color 206, indicator 202 is aligned with button 28 which displays the second color 208, and indicator 204 is aligned with button 30 displaying the third color 210. The buttons 26, 28, 30 are connected to actuation devices 70, so when the buttons 26, 28, 30 are depressed in direction 52, the actuating device 70 depress the respective circuit board switch 42, 44, 46.

Figure 9B:
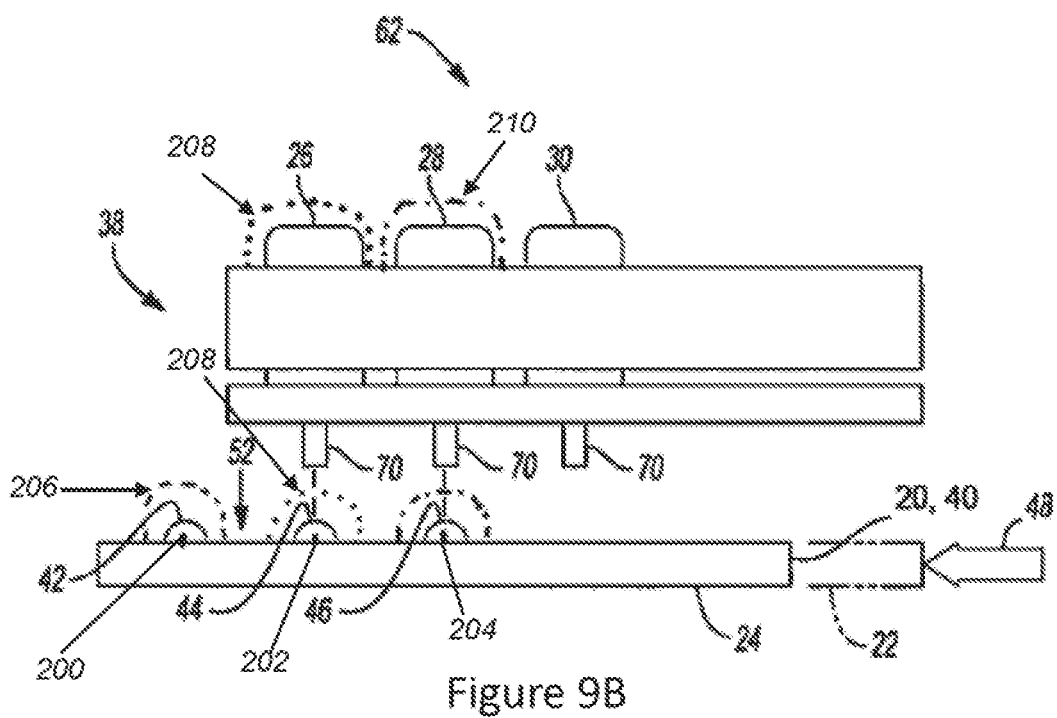
FIG. 9B is a perspective view of the device as a keyboard in a second position.

FIG. 9B illustrates a selector assembly 38, which is shown as a keyboard 62. The circuit board 40 of the keyboard 62 is shown moving in direction 48 from a first position 22 to a second position 24. In the second position 24 alignment of the circuit board switches 42, 44, 46 are changed relative to the first position 22. As shown activation button 26 is aligned with circuit board switch 44 and indicator 202, and activation button 28 is aligned with circuit board switch 46 and indicator 206. The second color 208 is now transmitted through button 26 and the third color 210 is now transmitted through button 28. Activation button 30 does not align with a circuit board switch and does not transmit a colored visual cue. When the activation buttons 26 and 28 are depressed in direction 52, the actuation device 70 will contact the circuit board switches 44 and 46. Similarly, Circuit board switch 42 does not align with an activation button, preventing the switch from being actuated.

FIG. 10A illustrates the selector assembly 38 in the first position 22. The selector assembly 38 is connected to the circuit board 40 through a leaf spring mechanism 96. In position one, the activation buttons 26, 28 are carried on the shuttle 20 and are aligned with the circuit board switches 42, 44 and indicators 200, 202. Indicator 200 displays a first color 206 through activation button 26 and indicator 202 displays a second color 208 through activation button 28. When activation buttons 26, 28 are depressed in the direction 52, the activation button 26, 28 will contact circuit board switches 42, 44, respectively. No activation buttons are aligned with circuit board switch 46 and indicator 206. The selector assembly includes a position change button 74 which is in communication with the leaf spring mechanism 96. The leaf spring mechanism 96 includes an actuator block 98 with a track 110, a plunger 108, and a leaf spring 104. The actuator block 98 attaches to the circuit board at region 106. The track 110 of the actuator block 98 has a top position 100 and a side position 102. The plunger 108 is connected to the position change button 74 and fits into the positions of the actuator block 100, 102 so when the position change button 74 is acted upon in direction 52, the plunger 108 moves from the top position 100 to the side position 102. When the plunger 108 moves, the leaf spring 104 can push the actuator block 98, which is connected to the circuit board 40 at 106, converting the device into position two. When the actuator block is moved from the first position to the second position, the circuit board 40 is moved relative to the activation buttons 26, 28. To move the device back to position one, the position change button can be actuated, causing the plunger to move about the track of the actuator block clockwise so that the plunger returns to position one.

FIG. 10B illustrates the selector assembly 38 in the second position 24. The selector assembly 38 is connected to the circuit board 40 through a leaf spring mechanism 96. The leaf spring mechanism 96 moves the circuit board 40 in direction 48, where the shuttle 20 holds the activation button 26 to align with the circuit board switch 46 and indicator 206 displaying a third color 210 through activation button 26. The second activation button 28 is misaligned with all of the circuit board switches 42, 44, 46 and displays no visual cue to a user. The first circuit board switch 42 and second circuit board switch 44 are not aligned with any of the activation buttons. When activation button 26 is depressed in the direction 52, it will contact the circuit board switch 46. The leaf spring assembly 96 converts the device from the first position 22 to the second position 24 through actuating the position change button 74 in the direction 52. The position change button depresses the plunger 108 causing the leaf spring mechanism 96 to relieve tension on the leaf spring 104 which expands and moves the circuit board 40 laterally by pushing the actuator block 98, which is connected to the circuit board 40 at 106, placing the device in the second position 24. When the position change button 74 is depressed, the plunger 108 moves along the track 110 of the actuator block 98 from the top position 100 to the side position 102. The circuit board 40 moves relative to the activation buttons 26, 28. The activation buttons 26, 28 are stationary relative the circuit board 40.

FIG. 11 illustrates the selector assembly 38 connected to the circuit board 40 through a short throw lever assembly 86 where the shuttle 20 holds the activation buttons 26, 28 aligns with the circuit board switches 42, 44 so that when the activation buttons 26, 28 are depressed in the direction 52, the activation buttons 26, 28 will contact the circuit board switches 42, 44 respectively. The circuit board switches 42, 44 have indicators 200 and 202 which display cues 206 and 208 corresponding to the function produced when each circuit board switch is actuated. The visual cues 206, 208 are transmitted through the activation buttons 26, 28 to a user. In this position, the third circuit board switch 46 and the third indicator 204 are not aligned with either of the activation buttons 26, 28. The short throw lever assembly 86 includes a lever 92, a fixed pivot point 88 that the lever rotates about, and moving pivot points 90 at the circuit board and the shuttle, respectively. The short throw lever assembly 86 converts the device between positions when moved in direction 94 by laterally moving the shuttle 20 holding the activation buttons 26 and 28 in direction 64 and the circuit board 40 in direction 48. The shuttle 20 and the circuit board 40 are connected by the lever 92 at moving pivot points 90, so when the short throw lever assembly 86 is acted upon, the lever 92 pivots about the fixed point 88, moving the shuttle 20, which holds the activation buttons 26 and 28, and the circuit board 40 into aligned or misaligned.

FIG. 12 illustrates the selector assembly 38 is connected to the circuit board 40 and shuttle 20 through a rack and pinion assembly 80. The rack and pinion assembly 80 helps convert the device between a first position and a second position by allowing the shuttle 20, carrying the activation buttons 26 and 28, to move relative to the circuit board 40. The rack and pinion assembly 80 includes a pinion gear 82 and a pair of rack gears 84, each attached to the circuit board 40 and the shuttle 20. As the pinion gear 82 rotates, the rack gears 84 laterally move the shuttle 20 in the 64 direction and circuit board 40 in the direction 48 placing the device into a second position, aligning or misaligning the activation buttons 26, 28 with the circuit board switches 42, 44, 46 and the indicators 200, 202, 204. In the position shown, the activation buttons 26 and 28 are aligned with circuit board switches 42 and 44 and indicators 200 and 202. The indicators 200 and 202 display visual cues 206 and 208 and transmit these visual cues through the activation buttons 26, 28 so that a user knows which function a button 26,28 will enable. When the activation buttons are depressed in the direction 52, activation button 26 will contact circuit board switch 42 producing a first electrical function and activation button 28 will contact circuit board switch 44 producing a second electrical function. Circuit board switch 46 and indicator 204 are not aligned with any activation buttons. A rack and pinion converts rotational movement to longitudinal movement or lateral movement.

Figure 13A:
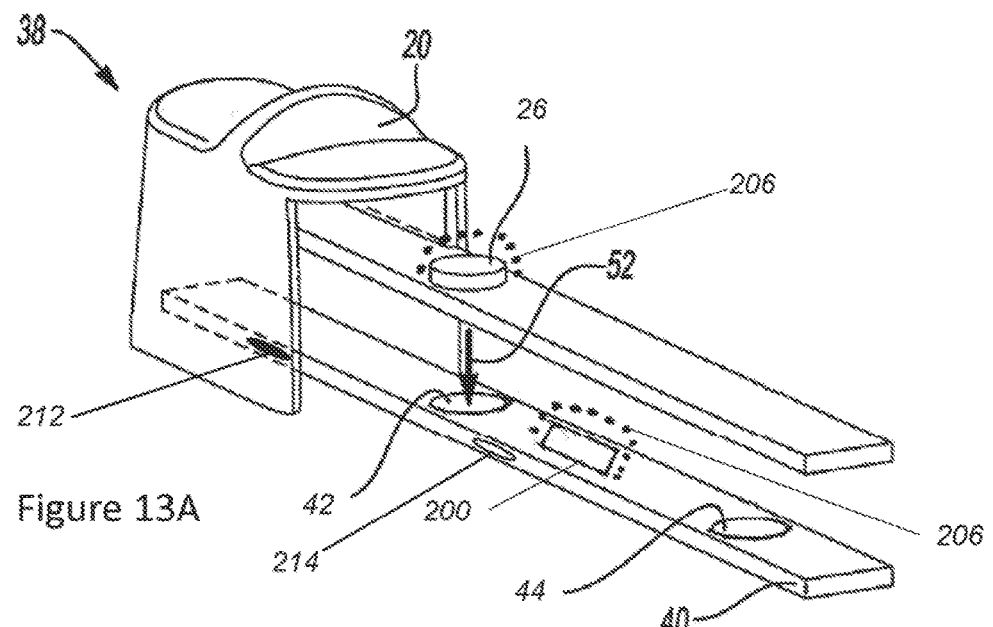
FIG. 13A is a perspective view of a selector assembly in a first position where the activation button is moveable relative to the circuit board and includes an indicator.

FIG. 13A illustrates a selector assembly 38 in a first position 22. The selector assembly includes a shuttle 20 carrying an activation button 26, connected with a circuit board 40. The circuit board 40 includes circuit board switches 42, 44, a changing indicator 200, and two position transmitters 212, 214. In the first position 22, the activation button 26 is aligned with the circuit board switch 42, configuring the device to perform a first function. The indicator transmits a first color 206 through the activation button 26 to a user, indicating that the first electrical function is selected. The first color 206 is produced when the first position transmitter 212 is actuated by the shuttle 20 in the first position 22, sending a signal to the circuit board 40 to power the first color 206. The second position transmitter is free from actuation.

Figure 13B:
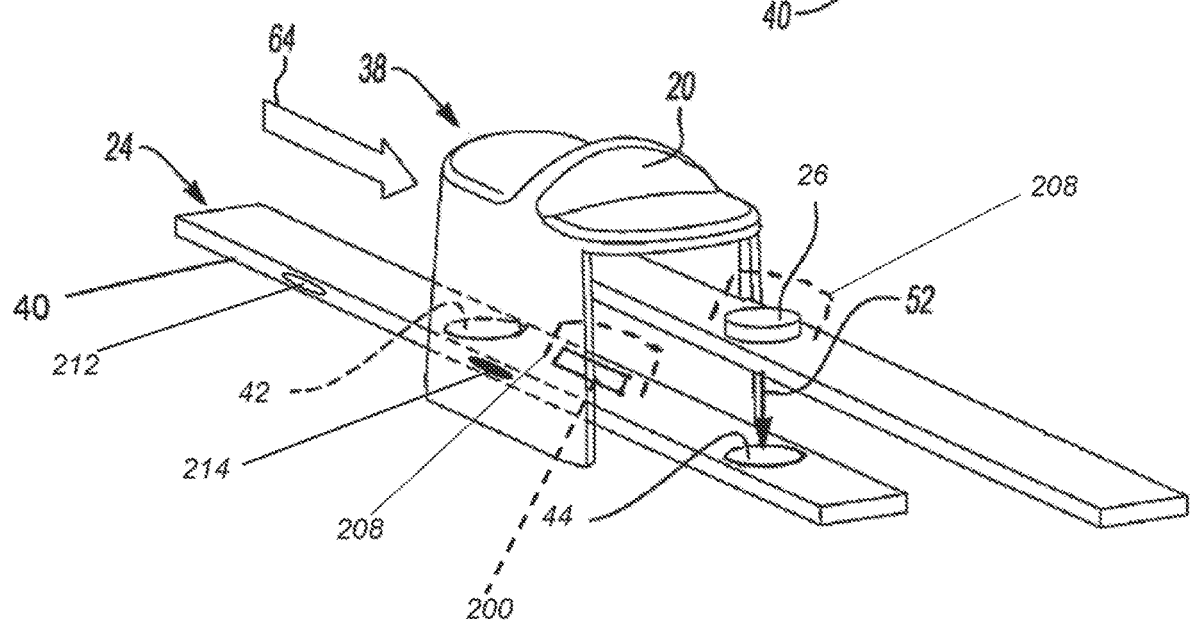
FIG. 13B is a perspective view of a selector assembly in a second position where the activation button is moveable relative to the circuit board and includes one an indicator.

FIG. 13B illustrates a selector assembly 38 of FIG. 13A in a second position 24. In the second position 24, the activation button 26 moves out of alignment with circuit board switch 42 and into alignment with circuit board switch 44, configuring the device to provide a second electrical function. Upon changing from the first position 22 to the second position 24, the second position transmitter 214 is actuated, sending a signal to the circuit board 40 to change the indicator from the first color 206 to a second color 208, indicating to a user that the device is now configured to perform the second function. In the second position 24, the first position transmitter is free from actuation.

Figure 14A:
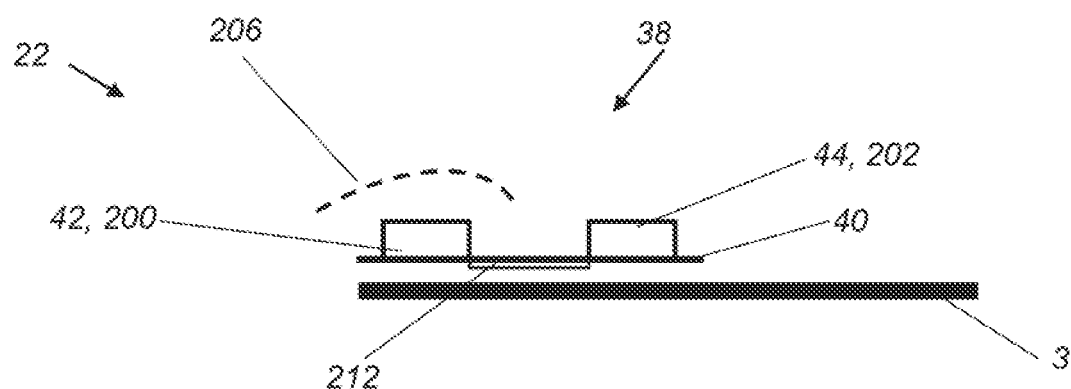
FIG. 14A is a perspective view of a circuit board in the first position relative to a body.

FIG. 14A illustrates a portion of the selector assembly 38 including a moveable circuit board 40. The circuit board 4 is moveable relative to the body 3. The circuit board carries a first circuit board switch 42 that is also the first indicator 200, and a second circuit board switch 44 that is also the second indicator 202. The circuit board also includes a position transmitter 212 which signals to the circuit board that the selector assembly 38 is in the first position, the circuit board sends power to the first indicator 200 to display the first visual cue 206. The second indicator 202 does not receive power in the first position 22.

Figure 14B:
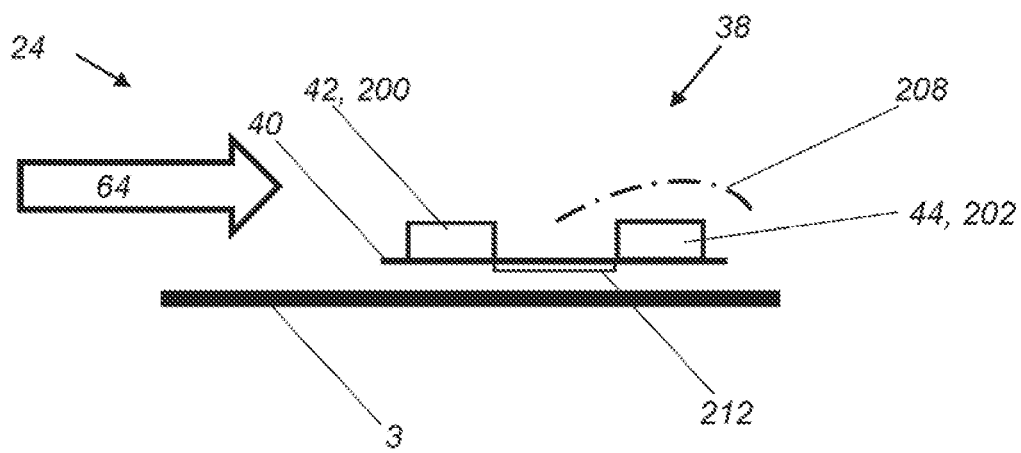
FIG. 14B is a perspective view of a circuit board in the second position relative to a body.

FIG. 14B illustrates the portion of the selector assembly 38 in the second position 24. The circuit board 40 is moved in direction 64 into the second position 24 from the first position 22 (not shown). The position transmitter 212 signals to the circuit board that the selector assembly 38 is in the second position so that the circuit board sends power to the second indicator 202 to display the second visual cue 208. The first indicator 200 does not receive power in the second position 24.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical device comprising:
   a. a device body;
   b. two or more functional states; and
   c. a selector assembly including:
      i. a shuttle that moves along the device body between at least a first position and a second position, the shuttle including a plurality of indicators and a circuit board with a plurality of switches coupled thereto such that movement of the shuttle causes a corresponding movement of the plurality of indicators and the circuit board with the plurality of switches; and
      ii. a button located on the device body;
   wherein the shuttle in the first position is configured to provide a first one of the two or more functional states, and in the second position is configured to provide a second one of the two or more functional states; and
   wherein a first one of the plurality of indicators communicates a first color through at least a portion of the button, corresponding to the first functional state, and a second one of the plurality of indicators communicates a second color through at least a portion of the button, corresponding to the second functional state.

2. The electrosurgical device of claim 1, wherein the plurality of indicators are located on the circuit board.

3. The electrosurgical device of claim 2, wherein the button is transparent.

4. The electrosurgical device of claim 2, wherein the plurality of indicators are colored circuit board switches.

5. The electrosurgical device of claim 2, wherein the plurality of indicators are light emitting devices.

6. The electrosurgical device of claim 1, wherein the first functional state is a monopolar current and the second functional state is a bipolar current;
   wherein the button aligns with a first switch of the plurality of circuit board switches when the selector assembly is in the first position so that upon actuation of the button, monopolar current is applied, and when the selector assembly is in the second position, the button aligns with a second switch of the plurality of circuit board switches so that upon actuation of the button, the bipolar current is applied.

7. The electrosurgical device of claim 1, wherein the selector assembly includes a rack and pinion assembly, the rack and pinion assembly includes a pinion gear between a first rack gear on the shuttle and a second rack gear on the circuit board;
   wherein the shuttle moves between the first position and the second position by rotating the pinion gear, moving the circuit board in an opposite direction of the shuttle.

8. An electrosurgical device comprising:
   a. two or more functional states;
   b. a shuttle that moves between at least a first position and a second position;
   c. a plurality of indicators including at least a first colored indicator and a second colored indicator; and
   d. a transparent button;
   wherein the shuttle is operable to move the first colored indicator into alignment with the transparent button so that a first color is visible through the transparent button, signaling that the electrosurgical device is in one of the two or more functional states; and
   wherein the shuttle is operable to move the second colored indicator into alignment with the transparent button so that a second color is visible through the transparent button, signaling that the electrosurgical device is in a different one of the two or more functional states.

9. The electrosurgical device of claim 8, wherein the indicators are color-changing light emitting devices.

10. The electrosurgical device of claim 9, wherein the electrosurgical device includes a circuit board with a plurality of switches.

11. The electrosurgical device of claim 10, wherein the shuttle moves a first switch into alignment with the transparent button indicating a first functional state of the two or more functional states, and the shuttle moves a second switch into alignment with the transparent button indicating a second functional state of the two or more functional states.

12. The electrosurgical device of claim 11, wherein the shuttle is in communication with the circuit board through a rack and pinion assembly, the rack and pinion assembly includes a pinion gear between a first rack gear on the shuttle and a second rack gear on the circuit board;
   wherein the shuttle moves between the first position and the second position by rotating the pinion gear, moving the circuit board in an opposite direction of the shuttle.

13. An electrosurgical device comprising:
   a. two or more functional states;
   b. a shuttle that is movable between at least a first position and a second position, the shuttle including a plurality of indicators and a circuit board with a plurality of switches coupled thereto such that movement of the shuttle causes a corresponding movement of the plurality of indicators and the circuit board with the plurality of switches; and c. a transparent button;

wherein the shuttle in the first position aligns a first switch of the plurality of switches with the transparent button so that the electrosurgical device is configured in a first functional state of the two or more functional states and a first indicator of the plurality of indicators transmits a first color through the transparent button;

wherein the shuttle in the second position aligns a second switch of the plurality of switches with the transparent button so that the electrosurgical device is configured in a second functional state of the two or more functional states and a second indicator of the plurality of indicators transmits a second color through the transparent button;

wherein the first and second indicators align with the transparent button in the first position and the second position, respectively, transmitting color through the transparent button to a user; and wherein the first color indicates that the electrosurgical device is in the first functional state, and the second color indicates that the electrosurgical device is in the second functional state.

14. The electrosurgical device of claim 13, wherein the electrosurgical device in the first functional state provides a monopolar current and in the second functional state provides a bipolar current.

* * * * *